United States Patent [19]

Horodysky et al.

[11] Patent Number: 4,541,941
[45] Date of Patent: Sep. 17, 1985

[54] MIXED BORATE ESTERS AND THEIR USE AS LUBRICANT AND FUEL ADDITIVES

[75] Inventors: Andrew G. Horodysky, Cherry Hill; Robert M. Gemmill, Jr., Pitman, both of N.J.

[73] Assignee: Mobil Oil Corporation, New York, N.Y.

[21] Appl. No.: 616,752

[22] Filed: Jun. 4, 1984

Related U.S. Application Data

[62] Division of Ser. No. 414,281, Sep. 3, 1982, abandoned.

[51] Int. Cl.$^4$ .............................................. C10M 1/54
[52] U.S. Cl. .................................. 252/49.6; 252/56 R
[58] Field of Search ............................ 252/49.6, 56 R

[56] References Cited

U.S. PATENT DOCUMENTS 2,979,459  4/1961  Darling et al. ...................... 252/49.6
2,989,468  6/1961  Darling et al. ...................... 252/49.6
4,406,802  9/1983  Horodysky et al. ............... 252/49.6

Primary Examiner—Jacqueline V. Howard
Attorney, Agent, or Firm—Alexander J. McKillop; Michael G. Gilman; Van D. Harrison, Jr.

[57] ABSTRACT

Lubricant and fuel compositions having unique fuel saving properties are obtained by adding to the lubricant or fuel a product made by reacting a boron compound with a mixture of vicinal diols and long chain alcohols or hydroxyl-containing carboxylate esters.

14 Claims, No Drawings

MIXED BORATE ESTERS AND THEIR USE AS LUBRICANT AND FUEL ADDITIVES

This is a division of copending application Ser. No. 414,281, filed Sept. 3, 1982, now abandoned.

BACKGROUND OF THE INVENTION

1. Field of the Invention

The invention relates to lubricant and liquid fuel compositions. In particular, it relates to the use of borated derivatives of, or mixtures of, hydrocarbyl vicinal diols with (1) hydroxyl-containing alkyl carboxylates, or (2) a long chain alcohol or mixtures of such alcohols in liquid fuels and lubricants to reduce friction and fuel consumption in internal combustion engines.

2. Discussion of the Prior Art

Alcohols are well known for their lubricity properties when formulated into lubricating oils and for their water-scavenging characteristics when blended into fuels. The use of vicinal hydroxyl-containing alkyl carboxylates such as glycerol monooleate have also found widespread use as lubricity additives. U.S. Pat. No. 2,788,326 discloses some of the esters suitable for the present invention, e.g., glycerol monooleate, as minor components of lubricating oil compositions. U.S. Pat. No. 3,235,498 discloses, among others, the same ester as just mentioned, as an additive to other oils. U.S. Pat. No. 2,443,578 teaches esters wherein the free hydroxyl is found in the acid portion, as for example in tartaric acid.

The above patents, as are numerous others, are directed to the use of such esters as additives. Other patents, such as U.S. Pats. Nos. 2,798,083; 2,820,014; 3,115,519; 3,282,971; and 3,309,318 as well as an article by R. R. Barnes et al. entitled "Synthetic Ester Lubricants" in Lubrication Engineering, August, 1975, pp. 454-457, teach lubricants prepared from polyhydric alcohols and acid containing no hydroxyl other than those associated with the acid function.

So far as is known, no effort has been made to employ the borated mixtures of this invention as fuel or lubricant additives. It is known that borated hydrocarbyl vicinal diols may be employed for such uses. For example, U.S. application Ser. No. 304,482, filed Sept. 22, 1981 teaches the use of these compounds in lubricants and fuels.

SUMMARY OF THE INVENTION

In accordance with the invention, there is provided a liquid fuel or lubricant composition comprising fuel or lubricant and a borated mixture of a hydrocarbyl vicinal diol and (1) a long chain alcohol or mixture of such alcohols or (2) a hydroxyl-containing aliphatic, preferably alkyl, carboxylate or mixtures of such hydroxyl-containing carboxylates. In such lubricant compositions, the product can be used in friction-reducing amounts, which can range from about 0.1% by weight to about 10% by weight. The borated products also have significantly greater friction-reducing properties, higher viscosity indices and good low temperature characteristics and solubility characteristics when used in low additive concentrations. As used herein, "hydrocarbyl" includes, but is not limited to decyl, dodecyl, tetradecyl, pentadecyl, hexadecyl, octadecyl, eicosyl and the like, and mixtures of such hydrocarbyl groups.

BACKGROUND OF THE INVENTION

It has now been found that the borated mixtures of this invention significantly improve friction-reducing properties and impart an antioxidant component to fuels and lubricants. In addition to the friction-reducing properties described, the borated esters possess much improved solubility characteristics, especially in synthetic fluids, over those of the non-borated derivatives. These borates are non-corrosive to copper, possess antioxidant and potential anti-fatigue characteristics.

The hydrocarbyl vicinal diols contemplated for use in this invention are hydrocarbyl diols having vicinal hydroxyls. Preferred are the aliphatic members, and more preferably the alkyl members. They have the formula:

R(—OH)$_2$ wherein R is a hydrocarbyl group containing 10 to 30 carbon atoms. R can be linear or branched, saturated or unsaturated with linear saturated members being preferred to maximize friction reduction. The two hydroxyl groups can be anywhere along the hydrocarbyl chain as long as they are on adjacent carbon atoms (vicinal), but the terminal diols are much preferred.

The vicinal diols can be synthesized using several methods known to the art such as that described in J. Am. Chem. Soc., 68, 1504 (1946) which involves the hydroxylation of 1-olefins with peracids. Vicinal diols can also be prepared by the peroxytrifluoroacetic acid method for the hydroxylation of olefins as described in J. Am. Chem. Soc., 76, 3472 (1954). Similar procedures can be found in U.S. 2,411,762, U.S. Pat. Nos. 2,457,329, 2,455,892.

The diols can also be prepared via catalytic epoxidation of an appropriate olefin followed by hydrolysis to form the appropriate vicinal diol.

The preferred borated vicinal diols contain 12 to 20 carbon atoms. Below a carbon number of 12 friction-reducing properties are significantly reduced. Above a carbon number of 20, solubility constraints become significant. More preferred are the $C_{14}$-$C_{17}$ hydrocarbyl groups in which solubility, frictional characteristics and other properties are maximized.

Among the diols contemplated for reaction with the boron compound are 1,2-hexanediol, 1,2-decanediol, 1,2-dodecanediol, 1,2-tetradecanediol, 1,2-pentadecanediol, 1,2-octadecanediol, 1,2-mixed $C_{15}$-$C_{18}$-alkanediols and mixtures thereof.

The hydrocarbyl carboxylate that may be used in the practice of this invention is one coming within the formula

$R^1(COOR^2)_n$ wherein $R^1$ is an aliphatic group or a hydroxy aliphatic group containing 2 to 10 carbon atoms, $R^2$ is an aliphatic or a hydroxy aliphatic group containing 8 to 20 carbon atoms and n is 1 to 3.

These esters may contain from 1 to 5 hydroxyl groups in the molecule. They may all be attached to $R^1$ or $R^2$ or they may be attached to $R^1$ and $R^2$ in varying proportions. Further, the hydroxyls can be at any position or positions along the aliphatic chain of $R^1$ or $R^2$. It will be understood that the esters contain at least one hydroxyl group.

These esters can be made by methods well known in the art. In general, they are made by reacting the desired acid or acyl halide and alcohol at temperatures and for times one skilled in the art can easily select.

Useful acid esters include such dihydroxyhydrocarbyl esters as 1,2-dihydroxypropyl oleate, sorbitan dioleate, mannitol dioleate, glycerol monooleate, glycerol dioleate, trimethylolpentane monooleate, trimethylolpentane dioleate, pentaerythritol monooleate, pentaerythritol dioleate, pentaerythritol trioleate, as well as others, including the stearates, isostearates and laurates.

The long chain alcohols or mixtures thereof that may be used for the purposes disclosed herein are alcohols of the formula $$R^3OH$$

wherein $R^3$ is a hydrocarbyl group containing from 10 to 20 carbon atoms. They include mixtures of such alcohols as oleyl alcohol, $C_{12}$–$C_{15}$ alkanols, $C_{14}$–$C_{15}$ alkanols, lauryl alcohol, stearyl alcohol, isostearyl alcohol, decanol, dodecanol, pentadecanol, and mixtures of such alcohols.

For maximum benefit, at least 10–20% of the total hydroxyl groups available for boration and up to 80% or more should be derived from the diol used or mixture of diols used.

The mixture prepared for boronation should contain an amount of the diol which will supply from about 10% to about 80% of the total hydroxyl groups available for boronation.

The boronated compound or compounds employed in this invention can be made using a single diol or mixtures of two or more diols or two or more carboxylates. Such mixtures can contain from about 5% to about 95% by weight of any one constituent, the other constituent(s) being selected such that it or they together comprise from about 95% to about 5% by weight of the mixture. Mixtures are often prepared to the single-member component.

Reaction with the boron compound, including boric oxide and others, such as those of the formula $$(R^4O)_xB(OH)_y$$

where $R^4$ is a $C_1$ to $C_6$ alkyl group, x is 0 to 3 and y is 0 to 3, the sum of x and y being 3, can be performed in the presence of an alcoholic solvent, such as butanol or pentanol, or a hydrocarbon solvent such as benzene, toluene or xylene, or mixtures of such solvents. Reaction temperatures of 90° C. to 260° C. or more can be used, but 110° to 200° C. is preferred. Reaction times can be 1 to 24 hours and more. Up to a stoichiometric amount of boric acid can be used, or an excess thereof can be used to produce a derivative containing from about 0.1% to about 10% of boron. At least 5 to 10% of the available hydroxyl groups should be borated to derive substantial beneficial effect. Conversely, a stoichiometric excess of boric acid (more than an equivalent amount of boronating agent compared to available hydroxyl groups) can also be charged to the reaction medium, resulting in a product containing the stated amount of boron. The compounds can also be borated with a trialkyl borate such as tributyl borate, often in the presence of boric acid. Preferred reaction temperatures for boration with the borate will range from about 180° C. to about 280° C. Times can be from about 2 to about 12 hours, or more, whether the mixture is borated or each is borated and then mixed.

As disclosed hereinabove, the borated esters are used with lubricating oils to the extent of from about 0.1% to about 10% by weight of the total composition. Furthermore, other additives, such as detergents, antioxidants, anti-wear agents viscosity index improvers, pour depressants, dispersants, and the like may be present. These can include phenates, sulfonates, succinimides, zinc dithiophosphates, polymers, calcium and magnesium salts and the like.

The lubricants contemplated for use with the esters herein disclosed include mineral and synthetic hydrocarbon oils of lubricating viscosity, mixtures of mineral oils and synthetic oils and greases from any of these, including mixtures. The synthetic hydrocarbon oils include long-chain alkanes such as cetanes and olefin polymers such as oligomers of hexane, octene, decene, and dodecene, etc. The mixtures of the invention are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acids, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylateacetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15, percent by weight of the total grease composition.

The liquid fuels contemplated include liquid hydrocarbon fuels such as fuel oils, diesel oils and gasolines and alcohol fuels such as methanol and ethanol or mixtures of these fuels.

In all reactions described hereinabove, a solvent is preferred. Solvents that can be used include the hydrocarbon solvents, such as toluene, benzene, xylene, and the like, alcohol solvents such as propanol, butanol, pentanol and the like, as well as mixtures of hydrocarbon solvents or alcohol solvents and mixtures of hydrocarbon and alcohol solvents.

Having described the invention in general terms, the following are offered to specifically illustrate the development. It is to be understood they are illustrations only and that the invention shall not be limited except as limited by the appended claims.

EXAMPLE 1

Borated Mixed 1,2-Hexadecanediol/$C_{12}$–$C_{15}$ Linear Alkanols

Approximately 52 g of mixed linear $C_{12}$–$C_{15}$ alkanols (commercially available as Shell Chemical Company's Neodol 25 having an average molecular weight of 208, a hydroxyl number of 270 and an approximate carbon number distribution of $C_{12}$-18%, $C_{13}$-30%, $C_{14}$-28%, $C_{15}$-24%), 65 g of 1,2-hexadecanediol and approximately 60 g of toluene were charged to a 1 liter reaction vessel equipped with agitator, heater and Dean-Stark tube with condenser. The contents were heated to about 70° C. to dissolve the solids and approximately 15.5 g of boric acid were added. The mixture was heated up to 160° C. until water evolution stopped over a period of 4½ hours. Approximately 12 ml. of water was removed by azeotropic distillation. The solvent was removed by vacuum distillation at 160° C. and the product was filtered at about 100° C. through diatomaceous earth. The product became a white, waxy solid after cooling.

EXAMPLE 2

Borated Mixed 1,2-Hexadecanediol/$C_{12}$–$C_{15}$ Linear Alkanols

Approximately 207 g of mixed linear $C_{12}$–$C_{15}$ alkanols (as described in Example 1), 258 g of 1,2-hexadecanediol and approximately 300 g of toluene were charged to a 2 liter reactior as described in Example 1. The reactants were heated to liquify them and approximately 63 g of boric acid were added. The mixture was heated up to 155° C. until water evolution stopped over a period of 4½ hours. Approximately 53 ml. of water were collected by azeotropic distillation. The solvent was removed by vacuum distillation at 155° C. and the product was filtered at about 110° C. through diatomaceous earth. The product became a white, waxy solid after cooling.

EXAMPLE 3

Borated Mixed 1,2-Hexadecanediol/$C_{12}$–$C_{15}$ Linear Alkanols

The procedure of Example 1 was followed but 709 g of 1,2-hexadecanediol, 570 g of $C_{12}$–$C_{15}$ linear alkanols, 300 g of toluene and 170 g of boric acid were used. A total of 145 ml. of water was collected by azeotropic distillation. The solvent was removed and the product was filtered through diatomaceous earth.

EXAMPLE 4

Borated Mixed 1,2-Hexadecanediol/Oleyl Alcohol

Approximately 54 g of oleyl alcohol, 51 g of 1,2-hexadecanediol and 100 g of toluene were reacted in a 1 liter reaction equipped as described in Example 1. The contents were heated to about 65° C. and 13 g of boric acid were added. The mixture was further heated up to 155° C. over a period of 4 hours until water evolution stopped. Approximately 11 ml. of water were collected by azeotropic distillation. The solvent was removed by vacuum distillation at 155° C. and the product was filtered at 90°–100° C. through diatomaceous earth.

EXAMPLE 5

Borated Mixed Glycerol Monooleate/1.2-Hexadecanediol

Approximately 92 g of glycerol monooleate (commercially available as 60/40 mixture of glycerol monoleate/glycerol diooleate), 52 g of 1,2-hexadecanediol and 100 g of toluene were charged to a reactor equipped as described in Example 1. The contents were heated to liquify and 11 g of boric acid were added. The mixture was further heated up to 150° C. over a period of 6 hours until water evolution stopped. Approximately 9 ml. of water collected. The solvent was removed by vacuum distillation at 150° C. and the product was filtered at about 100° C. through diatomaceous earth. The product became a waxy solid after cooling.

EXAMPLE 6

Borated Mixed 1,2-Dodecanediol/$C_{12}$–$C_{15}$ Linear Alkanols

Approximately 103 g of $C_{12}$–$C_{15}$ linear alkanols (as described in Example 1), 101 g of 1,2-dodecanediol and about 100 g of toluene were charged to a 1 liter reactor equipped as in Example 1. After warming to liquify, 31 g of boric acid was added. The mixture was heated up to 150° C. until water evolution stopped over a period of about 5 hours. The solvent was removed by vacuum distillation at 150° C. and the product was filtered hot through diatomaceous earth.

EXAMPLE 7

Borated Mixed 1,2 $C_{15}$-$C_{18}$ Alkanediols/Alkanols

Approximately 103 g of mixed linear $C_{12}$-$C_{15}$ (as described in Example 1), 133 g of mixed 1,2-$C_{15}$-$C_{18}$ alkanediols (commercially available as Viking Chemical Co. Vikol 15-18 and containing the following 1,2-alkanediols: 1,2-$C_{15}$, diol-28%; 1,2-$C_{16}$ diol-28%; 1,2-$C_{17}$ diol-28%; 1,2-$C_{18}$ diol-16%) and 100 g toluene were charged to a reactor equipped as described in Example 1. The reactants were warmed until fluid and approximately 31 g of boric acid were added. The mixture was heated up to 160° C. until water evolution stopped over a period of 5 hours. Approximately 28 ml. water were collected. The solvent was removed by vacuum distillation at 160° C. and the product was filtered through diatomaceous earth.

EVALUATION OF PRODUCTS

The compound were evaluated as friction modifiers in accordance with the following test.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

PROCEDURE

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4-8 microinches.

The data obtained are shown in Table 1. The data in Table 1 are reported as percent reduction in coefficient of friction at two speeds. The friction-reducing ester additives were evaluated in a fully formulated 5W-30 synthetic lubricating oil comprising an additive package including anti-oxidant, detergent and dispersant. The oil had the following general characteristics:

Viscosity 100° C.—11.0 cs
Viscosity 40° C.—58.2 cs
Viscosity Index—172

TABLE 1

| Example | Additive Conc. in Base Blend | % Reduction in Coefficient of Friction in LVFA at 5 Ft./Min. | 30 Ft./Min. |
|---|---|---|---|
| Base Fluid, SAE 5W-30 fully formulated engine oil | — | 0 | 0 |
| 1 | 2 | 46 | 37 |
|  | 1 | 41 | 35 |
| 2 | 2 | 44 | 35 |
|  | 1 | 41 | 34 |
|  | ½ | 38 | 28 |
|  | ¼ | 29 | 23 |
| 3 | 4 | 45 | 34 |
|  | 2½ | 50 | 39 |
|  | 1 | 45 | 37 |
| 4 | 2 | 43 | 32 |
| 5 | 2 | 43 | 34 |
| 6 | 2 | 32 | 22 |
| 7 | 2 | 40 | 33 |

CATALYTIC OXIDATION TEST

The mixed borates of Examples 1 to 7 were evaluated using the Catalytic Oxidation Test as shown in Table 2. Each of the examples evaluated demonstrated antioxidant properties, especially in terms of control of viscosity increase and increase in neutralization number.

The products of this invention were tested in lubricants, using as the base oil a 200″ solvent paraffinic neutral mineral oil. The test lubricant composition is subjected to a stream of air bubbled through the composition at a rate of 5 liters per hour at 325° F. for 40 hours. Present in the composition are metals commonly used as materials of engine construction, namely:

a. 15.6 sq. in. of sand-blasted iron wire,
b. 0.78 sq. in. of polished copper wire,
c. 0.87 sq. in. of polished aluminum wire, and
d. 0.167 sq. in. of polished lead surface.

Inhibitors for oil are rated on the basis of prevention of oil deterioration as measured by the increase in acid formation or neutralization number (NN) and kinematic viscosity (KV) occasioned by the oxidation. The results of the tests are reported in Table 2.

TABLE 2

| Additive of | Additive Conc. Wt. % | % Increase in Viscosity, KV at 100° C. | Neutralization Number | Lead Loss |
|---|---|---|---|---|
| Base Fluid, 200″ solvent parafinnic neutral lubricating oil | — | 67 | 3.62 | −1.2 |
| Example 1 | 1 | 24 | 2.16 | 0.2 |
|  | 3 | 41 | 2.50 | 0.5 |
| Example 2 | 1 | 29 | 2.00 | 0.5 |
|  | 3 | 47 | 2.42 | 0.2 |
| Example 3 | 1 | 17 | 2.09 | 0.9 |
|  | 3 | 47 | 2.53 | 0.3 |
| Example 4 | 1 | 19 | 1.94 | 0.1 |
|  | 3 | 26 | 2.12 | 0.1 |
| Example 5 | 1 | 15 | 2.22 | 0.0 |
|  | 3 | 27 | 1.95 | 0.5 |
| Example 6 | 1 | 32 | 2.99 | 0.0 |
|  | 3 | 40 | 2.85 | 0.3 |
| Example 7 | 1 | 20 | 1.92 | 0.2 |
|  | 3 | 19 | 2.55 | 0.3 |

The results clearly show the effectiveness of the borates at controlling viscosity increase and neutralization number increase under somewhat severe oxidation conditions.

ENGINE TEST

The product of Example 3 was blended at the 2½% concentration level into a fully formulated automotive engine oil containing detergent/dispersant/inhibitor package and evaluated for bearing corrosion inhibiting properties.

The oxidation test used is a high temperature oxidation test for determining bearing corrosion and deposit forming characteristics. The test employs a CLRL-38 single cylinder engine which is run with the test composition for 40 hours (or for 80, 120, etc. hours for extended tests). The engine speed is about 315 RPM. In testing our compounds, the engine was run for 40 and 80 hours at an approximate load adjusted to give an air/fuel ratio of about 14:1 and a fuel flow of about 4.75 lbs/hour.

Both 40-hour single length and extraordinarily severe 80-hour double length test results were satisfactory, as the results in Table 3 show.

TABLE 3

|  | Bearing Wt. Loss, mg 40 Max. |
|---|---|
| 40 Hours | 17 |
| 80 Hours, Double Length | 18 |

We claim:

1. A lubricant composition comprising a major proportion of a lubricating oil or grease and a friction-reducing amount of a borated mixture of a hydrocarbyl vicinal diol, or mixtures thereof, and a hydroxyl-containing aliphatic carboxylate or mixture of said carboxylates.

2. The composition of claim 1 wherein the diol has the formula $$R(OH)_2$$

wherein R is a hydrocarbyl group containing 10 to 30 carbon atoms.

3. The composition of claim 2 wherein the hydrocarbyl group is an alkyl group.

4. The composition of claim 3 wherein the alkyl group is a hexyl, decyl, dodecyl, tetradecyl, pentadecyl, octadecyl or mixed $C_{15}$–$C_{18}$ alkyl group.

5. The composition of claim 1 wherein the carboxylate has the formula $$R^1(COOR^2)_n$$

wherein $R^1$ is an aliphatic or hydroxy aliphatic group containing 3 to 10 carbon atoms and $R^2$ is an aliphatic or hydroxy aliphatic group containing 8 to 20 carbon atoms and n is 1 to 3, there being present in the carboxylate at least one hydroxy group.

6. The composition of claim 5 wherein the carboxylate is 1,2-dihydroxypropyl monooleate, sorbitan dioleate, mannitol dioleate, glycerol monooleate, glycerol dioleate, trimethylolpentane monooleate, trimethylolpentane dioleate, pentaerythritol monooleate, pentaerythritol dioleate or pentaerythritol trioleate.

7. The composition of claim 1 wherein the mixture for boration is borated with boric oxide or a compound of the formula $$(R^4O)_xB(OH)_y$$

wherein $R^4$ is a $C_1$ to $C_6$ alkyl group, x is 0 to 3 and y is 0 to 3 their sum being 3.

8. The composition of claim 1 wherein the mixture for boration is borated with boric acid.

9. The composition of claim 1 wherein the mixture for boration is a mixture of glycerol monooleate and 1,2-hexadecanediol and the borating agent is boric acid.

10. The composition of claim 1 wherein the lubricating oil is (1) a mineral lubricating oil, (2) a synthetic lubricating oil or a mixture of such oils, (3) a mixture of (1) and (2), or (4) a grease of any of these.

11. The composition of claim 10 wherein the lubricating oil is a mineral oil.

12. The composition of claim 10 wherein the lubricating oil is a synthetic oil.

13. The composition of claim 1 wherein the lubricant is a grease.

14. The composition of claim 1 wherein the lubricant is a mixture of mineral and synthetic oils.

* * * * *